(12) United States Patent
Khairkhahan et al.

(10) Patent No.: US 7,582,051 B2
(45) Date of Patent: Sep. 1, 2009

(54) PERIPHERAL SEAL FOR A VENTRICULAR PARTITIONING DEVICE

(75) Inventors: Alexander Khairkhahan, Palo Alto, CA (US); Hugh R. Sharkey, Redwood City, CA (US); Serjan D. Nikolic, San Francisco, CA (US); Branislav Radovancevic, Houston, TX (US)

(73) Assignee: CardioKinetix, Inc., Menlo Park, CA (US)

( * ) Notice: Subject to any disclaimer, the term of this patent is extended or adjusted under 35 U.S.C. 154(b) by 482 days.

(21) Appl. No.: 11/151,164

(22) Filed: Jun. 10, 2005

(65) Prior Publication Data

US 2006/0281965 A1    Dec. 14, 2006

(51) Int. Cl.
*A61F 2/00* (2006.01)
(52) U.S. Cl. .................. 600/16; 600/37; 623/3.16
(58) Field of Classification Search .............. 600/16, 600/37; 606/200; 623/3.16
See application file for complete search history.

(56) References Cited

U.S. PATENT DOCUMENTS

| | | | |
|---|---|---|---|
| 3,874,388 A * | 4/1975 | King et al. | 606/232 |
| 4,007,743 A | 2/1977 | Blake | |
| 4,425,908 A | 1/1984 | Simon | |
| 4,619,246 A | 10/1986 | Molgaard-Nielsen et al. | |
| 4,685,446 A | 8/1987 | Choy | |
| 4,710,192 A | 12/1987 | Liotta et al. | |
| 4,832,055 A | 5/1989 | Palestrant | |
| 4,917,089 A | 4/1990 | Sideris | |
| 5,104,399 A | 4/1992 | Lazarus | |
| 5,192,301 A * | 3/1993 | Kamiya et al. | 606/213 |
| 5,192,314 A | 3/1993 | Daskalakis et al. | |

(Continued)

FOREIGN PATENT DOCUMENTS

WO    WO 00/27292    5/2000

(Continued)

OTHER PUBLICATIONS

Khairkhahan, et al., U.S. Appl. No. 10/436,959, entitled "System for improving cardiac function," filed May 12, 2003 (WSGR Reference No. 33108-701.505).

(Continued)

*Primary Examiner*—Carl H Layno
*Assistant Examiner*—Eugene T Wu
(74) *Attorney, Agent, or Firm*—Shay Glenn LLP

(57) ABSTRACT

A partitioning device for separating a patient's heart chamber into a productive portion and a non-productive portion which is suitable for treating patients with heart disease, particularly congestive heart failure. The partitioning device has a reinforced membrane with outwardly biased members to help seal the periphery of the membrane against the wall of the patient's heart chamber. In one embodiment, the outwardly biased member is an expansive strand that extends between adjacent ribs of an expandable frame which reinforces the membrane. In another embodiment, the outwardly biased member is a hydrophilic body such as foam which swells upon contact with body fluid such as blood in the heart chamber. The reinforced membrane has a central hub with a distally extending support stem with a plurality of feet which extend radially from a centerline axis and preferably have ends that are aligned in a common plane. The ends of the pods which extend radially away from the centerline axis may be interconnected by flexible struts and/or webs.

44 Claims, 13 Drawing Sheets

U.S. PATENT DOCUMENTS

| | | |
|---|---|---|
| 5,375,612 A | 12/1994 | Cottenceau et al. |
| 5,385,156 A | 1/1995 | Oliva |
| 5,425,744 A | 6/1995 | Fagan et al. |
| 5,433,727 A | 7/1995 | Sideris |
| 5,451,235 A | 9/1995 | Lock et al. |
| 5,496,277 A | 3/1996 | Termin et al. |
| 5,527,337 A | 6/1996 | Stack et al. |
| 5,527,338 A | 6/1996 | Purdy |
| 5,549,621 A | 8/1996 | Bessler et al. |
| 5,578,069 A | 11/1996 | Miner, II |
| 5,634,936 A | 6/1997 | Linden et al. |
| 5,634,942 A | 6/1997 | Chevillon et al. |
| 5,702,343 A | 12/1997 | Alferness |
| 5,709,707 A | 1/1998 | Lock et al. |
| 5,791,231 A | 8/1998 | Cohn et al. |
| 5,797,849 A | 8/1998 | Vesely et al. |
| 5,797,960 A | 8/1998 | Stevens et al. |
| 5,829,447 A | 11/1998 | Stevens et al. |
| 5,833,698 A | 11/1998 | Hinchliffe et al. |
| 5,836,968 A | 11/1998 | Simon et al. |
| 5,843,170 A | 12/1998 | Ahn |
| 5,861,003 A | 1/1999 | Latson et al. |
| 5,865,730 A | 2/1999 | Fox et al. |
| 5,865,791 A | 2/1999 | Whayne et al. |
| 5,871,017 A | 2/1999 | Mayer |
| 5,875,782 A | 3/1999 | Ferrari et al. |
| 5,876,325 A | 3/1999 | Mizuno et al. |
| 5,876,449 A | 3/1999 | Starck et al. |
| 5,879,366 A | 3/1999 | Shaw et al. |
| 5,882,340 A | 3/1999 | Yoon |
| 5,910,150 A | 6/1999 | Saadat |
| 5,916,145 A | 6/1999 | Chu et al. |
| 5,924,424 A | 7/1999 | Stevens et al. |
| 5,925,062 A | 7/1999 | Purdy |
| 5,925,076 A | 7/1999 | Inoue |
| 5,928,260 A | 7/1999 | Chin et al. |
| 5,961,440 A | 10/1999 | Schweich, Jr. et al. |
| 5,961,539 A | 10/1999 | Northrup, III et al. |
| 5,984,917 A | 11/1999 | Fleischman et al. |
| 6,024,096 A | 2/2000 | Buckberg |
| 6,024,756 A | 2/2000 | Huebsch et al. |
| 6,045,497 A | 4/2000 | Schweich et al. |
| 6,059,715 A | 5/2000 | Schweich et al. |
| 6,076,013 A | 6/2000 | Brennan et al. |
| 6,077,214 A | 6/2000 | Mortier et al. |
| 6,077,218 A | 6/2000 | Alferness |
| 6,093,199 A | 7/2000 | Brown et al. |
| 6,095,968 A | 8/2000 | Snyders |
| 6,096,347 A | 8/2000 | Geddes et al. |
| 6,099,832 A | 8/2000 | Mickle et al. |
| 6,102,887 A | 8/2000 | Altman |
| 6,125,852 A | 10/2000 | Stevens et al. |
| 6,132,438 A | 10/2000 | Fleischman et al. |
| 6,152,144 A * | 11/2000 | Lesh et al. ................ 128/898 |
| 6,161,543 A | 12/2000 | Cox et al. |
| 6,193,731 B1 | 2/2001 | Oppelt et al. |
| 6,221,092 B1 | 4/2001 | Koike et al. |
| 6,231,561 B1 | 5/2001 | Frazier et al. |
| 6,258,021 B1 | 7/2001 | Wilk |
| 6,267,772 B1 | 7/2001 | Mulhauser et al. |
| 6,290,674 B1 | 9/2001 | Roue et al. |
| 6,312,446 B1 | 11/2001 | Huebsch et al. |
| 6,328,727 B1 | 12/2001 | Frazier et al. |
| 6,334,864 B1 | 1/2002 | Amplatz et al. |
| 6,343,605 B1 | 2/2002 | Lafontaine |
| 6,348,068 B1 | 2/2002 | Campbell et al. |
| 6,355,052 B1 | 3/2002 | Neuss et al. |
| 6,360,749 B1 | 3/2002 | Jayaraman |
| 6,364,896 B1 | 4/2002 | Addis |
| 6,387,042 B1 | 5/2002 | Herrero |
| 6,406,420 B1 | 6/2002 | McCarthy et al. |
| 6,419,669 B1 | 7/2002 | Frazier et al. |
| 6,436,088 B2 | 8/2002 | Frazier et al. |
| 6,450,171 B1 | 9/2002 | Buckberg et al. |
| 6,482,228 B1 | 11/2002 | Norred |
| 6,506,204 B2 | 1/2003 | Mazzocchi |
| 6,511,496 B1 | 1/2003 | Huter et al. |
| 6,537,198 B1 | 3/2003 | Vidlund et al. |
| 6,551,303 B1 | 4/2003 | Van Tassel et al. |
| 6,592,608 B2 | 7/2003 | Fisher et al. |
| 6,652,555 B1 | 11/2003 | VanTassel et al. |
| 6,685,627 B2 | 2/2004 | Jayaraman |
| 6,730,108 B2 | 5/2004 | Van Tassel et al. |
| 6,852,076 B2 | 2/2005 | Nikolic et al. |
| 6,959,711 B2 | 11/2005 | Murphy et al. |
| 6,994,093 B2 | 2/2006 | Murphy et al. |
| 7,144,363 B2 | 12/2006 | Pai et al. |
| 7,320,665 B2 | 1/2008 | Vijay |
| 2001/0014800 A1 | 8/2001 | Frazier et al. |
| 2002/0019580 A1 | 2/2002 | Lau et al. |
| 2002/0026092 A1 | 2/2002 | Buckberg et al. |
| 2002/0028981 A1 | 3/2002 | Lau et al. |
| 2002/0032481 A1 | 3/2002 | Gabbay |
| 2002/0055767 A1 | 5/2002 | Forde et al. |
| 2002/0055775 A1 | 5/2002 | Carpentier et al. |
| 2002/0111647 A1* | 8/2002 | Khairkhahan et al. ....... 606/200 |
| 2002/0133227 A1 | 9/2002 | Murphy et al. |
| 2002/0161394 A1 | 10/2002 | Macoviak et al. |
| 2002/0169359 A1 | 11/2002 | McCarthy et al. |
| 2002/0169360 A1 | 11/2002 | Taylor et al. |
| 2002/0188170 A1 | 12/2002 | Santamore et al. |
| 2003/0045896 A1 | 3/2003 | Murphy et al. |
| 2003/0050682 A1 | 3/2003 | Sharkey et al. |
| 2003/0050685 A1* | 3/2003 | Nikolic et al. ............. 623/1.11 |
| 2003/0105384 A1 | 6/2003 | Sharkey et al. |
| 2003/0109770 A1 | 6/2003 | Sharkey et al. |
| 2003/0120337 A1 | 6/2003 | Van Tassel et al. |
| 2003/0149333 A1 | 8/2003 | Alferness |
| 2003/0181942 A1 | 9/2003 | Sutton et al. |
| 2003/0220667 A1 | 11/2003 | Van Der Burg et al. |
| 2004/0002626 A1 | 1/2004 | Feld et al. |
| 2004/0034366 A1* | 2/2004 | van der Burg et al. ....... 606/119 |
| 2004/0044361 A1* | 3/2004 | Frazier et al. ............... 606/200 |
| 2004/0064014 A1 | 4/2004 | Melvin et al. |
| 2004/0260331 A1 | 12/2004 | D'Aquanni et al. |
| 2004/0267378 A1 | 12/2004 | Gazi et al. |
| 2005/0007031 A1 | 1/2005 | Hyder |
| 2005/0015109 A1* | 1/2005 | Lichtenstein ................ 606/200 |
| 2005/0096498 A1 | 5/2005 | Houser et al. |
| 2005/0113861 A1 | 5/2005 | Corcoran et al. |
| 2005/0154252 A1 | 7/2005 | Sharkey et al. |
| 2005/0177180 A1 | 8/2005 | Kaganov et al. |
| 2005/0197716 A1 | 9/2005 | Sharkey et al. |
| 2005/0216052 A1 | 9/2005 | Mazzocchi et al. |
| 2005/0228434 A1 | 10/2005 | Amplatz et al. |
| 2006/0014998 A1 | 1/2006 | Sharkey et al. |
| 2006/0025800 A1 | 2/2006 | Suresh |
| 2006/0030881 A1 | 2/2006 | Sharkey et al. |
| 2006/0264980 A1* | 11/2006 | Khairkhahan et al. ....... 606/153 |
| 2006/0276684 A1 | 12/2006 | Speziali |

FOREIGN PATENT DOCUMENTS

| | | |
|---|---|---|
| WO | WO 01/30266 | 5/2001 |
| WO | WO 01/78625 A1 | 10/2001 |
| WO | WO 02/30335 A2 | 4/2002 |
| WO | WO 02/071977 A2 | 9/2002 |
| WO | WO 03/007778 A | 1/2003 |
| WO | WO 2004/012629 A | 2/2004 |
| WO | WO 2004/100803 | 11/2004 |

| | | |
|---|---|---|
| WO | WO 2005/007031 | 1/2005 |

OTHER PUBLICATIONS

Sharkey, et al., U.S. Appl. No. 11/199,633, entitled "Method for treating myocardial rupture," filed Aug. 9, 2005 (WSGR Reference No. 33108-706.201).

Khairkhahan, et al; U.S. Appl. No. 11/801,075, entitled "System for improving cardiac function," filed May 7, 2007 (SLG # 10078-701.302).

Khairkhahan et al; U.S. Appl. No. 11/800,998, entitled "System for improving cardiac function," filed May 7, 2007 (SLG # 10078-701.400).

Nikolic et al; U.S. Appl. No. 11/640,469, entitled "Cardiac device and methods of use thereof," filed Dec. 14, 2006 (SLG # 10078-701.508).

Tetsuji Kawata et al., "Systolic and Diastolic Function After Patch Reconstruction of Left Ventricular Aneurysms", Ann. Thorac. Surg. 59, pp. 403-407, 1995.

Vincent Dor, "The Treatment of Refractory Ischemic Ventricular Tachycardia by Endoventricular Patch Plasty Reconstructin of the Left Ventricle", Seminars in Thoracic and Cardiovascular Surgery, vol. 9, No. 2, pp. 146-155, Apr. 1997.

Daniel Giorgio Di Mattia et al., "Surgical treatment of left ventricular post-infarction aneurysm with endoventriculoplasty: late clinical and functional results", European Journal of Cardio-thoracic Surgery 15, pp. 413-419, 1999.

T Katsumata et al., "An objective appraisal of partial left ventriculectomy for heart failure", Journal of Congestive Heart Failure and Circulator Support, pp. 97-106, 1999.

Vincent Dor, "Surgery for left ventricular aneurysm", Current Opinion in Cardiology, Current Science, pp. 773-780, 1990.

Vincent Dor et al., "Ventricular remodeling in coronary artery disease", Current Opinion in Cardiology, Rapid Science Publishers, pp. 533-537, 1997.

AGA Medical Corporation, www.amplatzer.com/products, "The Muscular VSD Occluder" and "The Septal Occluder" device descriptions, Apr. 3, 2002.

Gore Medical, www.goremedical.com, "Helex Septal Occluder" product description, Apr. 3, 2002.

Khairkhahan et al; U.S. Appl. No. 11/860,438 entitled "Laminar ventricular partitioning device," filed Sep. 24, 2007.

Nikolic, et al., U.S. Appl. No. 12/129,443 entitled "Therapeutic methods and devices following myocardial infarction," filed May 29, 2008.

Khairkhahan et al; U.S. Appl. No. 12/125,015 entitled "Ventricular partitioning device," filed May 21, 2008.

* cited by examiner

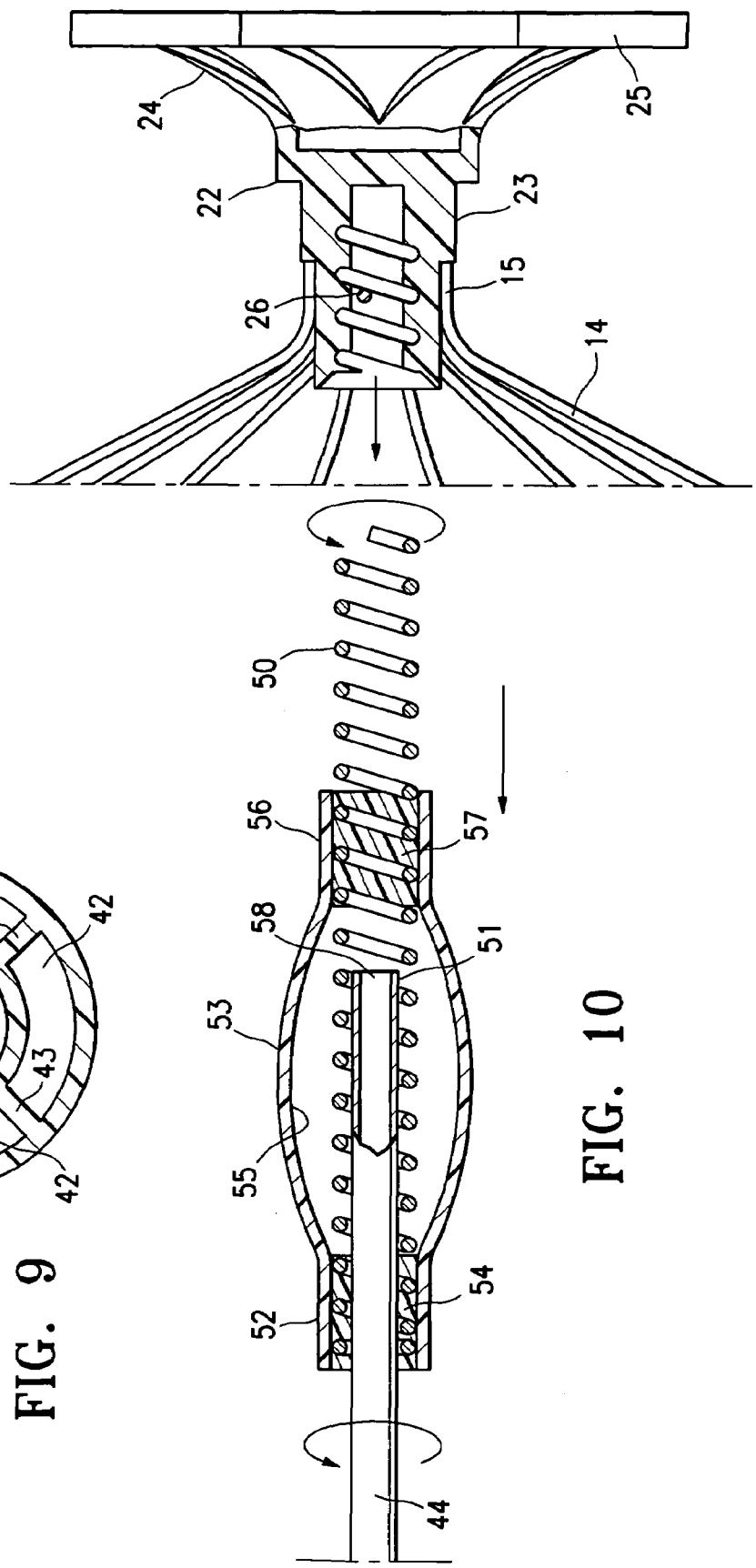

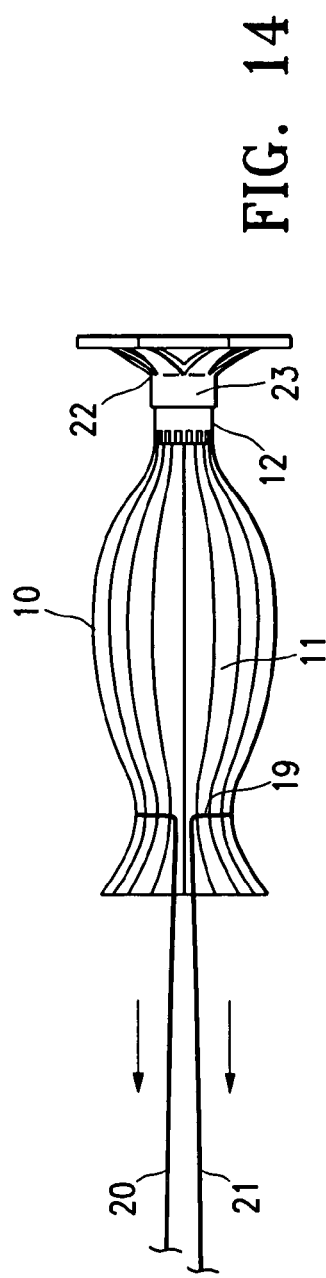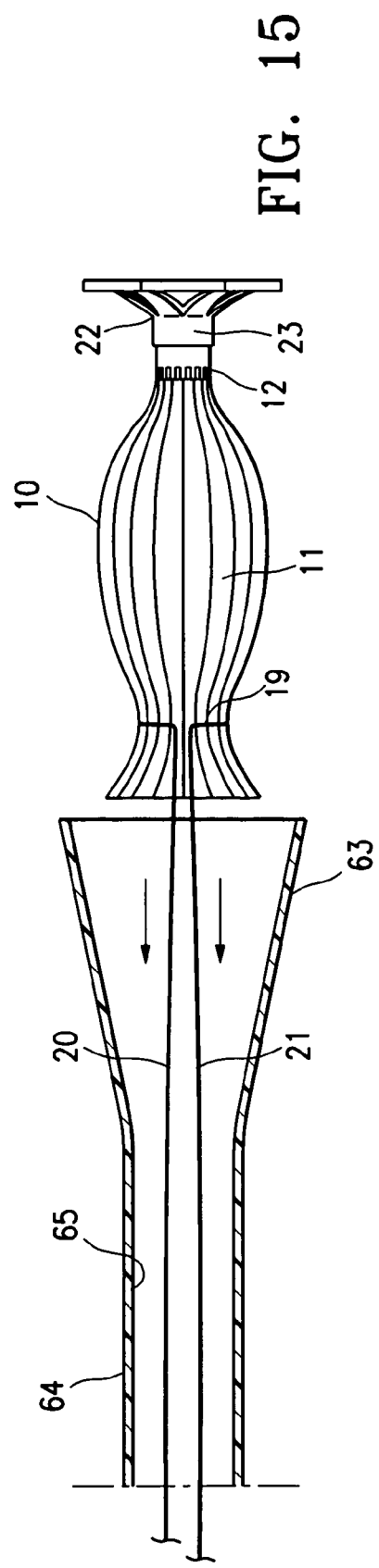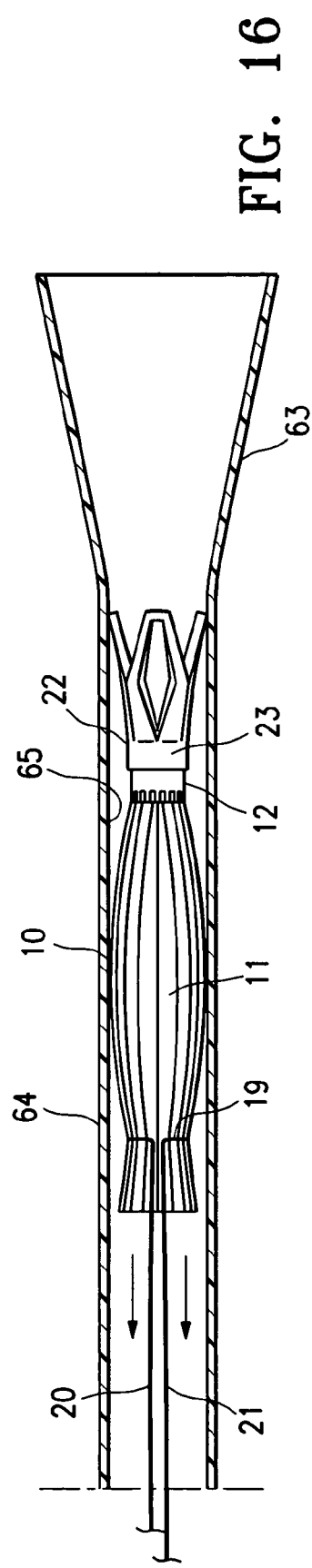
FIG. 14
FIG. 15
FIG. 16

PERIPHERAL SEAL FOR A VENTRICULAR PARTITIONING DEVICE

FIELD OF THE INVENTION

The present invention relates generally to the field of treating heart disease, particularly congestive heart failure, and more specifically, to a device and method for partitioning a patient's heart chamber and a system for delivering the treatment device.

BACKGROUND OF THE INVENTION

Congestive heart failure (CHF) is characterized by a progressive enlargement of the heart, particularly the left ventricle and is a major cause of death and disability in the United States. Approximately 550,000 new cases occur annually in the U.S. alone. As the patient's heart enlarges, it cannot efficiently pump blood forward with each heart beat. In time, the heart becomes so enlarged the heart becomes ineffective as a pump and cannot adequately supply blood to the body. Even in healthy hearts only a certain percentage of the blood in a patient's left ventricle is pumped out or ejected from the chamber during each stroke of the heart. The pumped percentage, commonly referred to as the "ejection fraction", is typically about sixty percent for a healthy heart. A patient with congestive heart failure can have an ejection fraction of less than 40% and sometimes much lower. As a result of the low ejection fraction, a patient with congestive heart failure is fatigued, unable to perform even simple tasks requiring exertion and experiences pain and discomfort. Further, as the heart enlarges, the internal heart valves such as the mitral valve cannot adequately close. An incompetent mitral valve allows regurgitation of blood from the left ventricle back into the left atrium, further reducing the heart's ability to pump blood forwardly.

Congestive heart failure can result from a variety of conditions, including viral infections, incompetent heart valves (e.g. mitral valve), ischemic conditions in the heart wall or a combination of these conditions. Prolonged ischemia and occlusion of coronary arteries can result in myocardial tissue in the ventricular wall dying and becoming scar tissue. Once the myocardial tissue dies, it is less contractile (sometimes non-contractile) and no longer contributes to the pumping action of the heart. It is referred to as hypokinetic or akinetic. As the disease progresses, a local area of compromised myocardium may bulge out during the heart contractions, further decreasing the heart's ability to pump blood and further reducing the ejection fraction. In this instance, the heart wall is referred to as dyskinetic. The dyskinetic region of the heart wall may stretch and eventually form an aneurysmic bulge.

Patients suffering from congestive heart failure are commonly grouped into four classes, Classes I, II, III and IV. In the early stages, Classes I and II, drug therapy is presently the most common treatment. Drug therapy typically treats the symptoms of the disease and may slow the progression of the disease, but it can not cure the disease. Presently, the only permanent treatment for congestive heart disease is heart transplantation, but heart transplant procedures are very risky, extremely invasive and expensive and are performed on a small percentage of patients. Many patient's do not qualify for heart transplant for failure to meet any one of a number of qualifying criteria, and, furthermore, there are not enough hearts available for transplant to meet the needs of CHF patients who do qualify.

Substantial effort has been made to find alternative treatments for congestive heart disease. For example, surgical procedures have been developed to dissect and remove weakened portions of the ventricular wall in order to reduce heart volume. This procedure is highly invasive, risky and expensive and is commonly only done in conjunction with other procedures (such as heart valve replacement or coronary artery by-pass graft). Additionally, the surgical treatment is usually only offered to Class III and IV patients and, accordingly, is not an option for most patients facing ineffective drug treatment. Finally, if the procedure fails, emergency heart transplant is the only presently available option.

Mechanical assist devices have been developed as intermediate procedures for treating congestive heart disease. Such devices include left ventricular assist devices and total artificial hearts. A left ventricular assist device includes a mechanical pump for increasing blood flow from the left ventricle into the aorta. Total artificial heart devices, such as the Jarvik heart, are usually used only as temporary measures while a patient awaits a donor heart for transplant.

Recently, improvements have been made in treating patient's with CHF by implanting pacing leads in both sides of the heart in order to coordinate the contraction of both ventricles of the heart. This technique has been shown to improve hemodynamic performance and can result in increased ejection fraction from the right ventricle to the patient's lungs and the ejection fraction from the left ventricle to the patient's aorta. While this procedure has been found to be successful in providing some relief from CHF symptoms and slowed the progression of the disease, it has not been able to stop the disease and is only indicated in patients with ventricular dissynchrony.

Other efforts to treat CHF include the use of an elastic support, such as an artificial elastic sock, placed around the heart to prevent further deleterious remodeling.

SUMMARY OF THE INVENTION

The present invention is directed to a ventricular partitioning device and method of employing the device in the treatment of a patient with heart disease and particularly congestive heart failure (CHF). Specifically, the device partitions a chamber of the patient's heart into a main productive portion and a secondary non-productive portion. This partitioning reduces the total volume of the heart chamber, reduces the stress applied to weakened tissue of the patient's heart wall and, as a result, improves the ejection fraction thereof. Moreover, the expansive nature of the device improves the diastolic function of the patient's heart.

A partitioning device embodying features of the invention has a reinforced partitioning component with a concave, pressure receiving surface which defines in part the main productive portion of the partitioned heart chamber when secured within the patient's heart chamber. The reinforced partitioning component has a flexible membrane that forms the pressure receiving surface. The partitioning component is preferably reinforced by a radially expandable frame component formed of a plurality of ribs. The ribs of the expandable frame have secured distal ends, which are preferably secured to a central hub, and free proximal ends. The distal ends of the ribs are preferably secured to the central hub to facilitate radial self expansion of the free proximal ends of the ribs away from a centerline axis. The distal ends of the ribs may be pivotally mounted to the hub and biased outwardly or fixed to the hub. The ribs are preferably formed of material such as superelastic NiTi alloy which allows for compressing the free proximal ends of the ribs toward a centerline axis into a contracted configuration for delivery and self expansion when released for deployment to an expanded configuration when released within the patient's heart chamber.

The free proximal ends of the ribs are configured to engage and preferably penetrate the tissue lining the heart chamber to be partitioned so as to secure the peripheral edge of the partitioning component to the heart wall and fix the partitioning component within the chamber so as to partition the chamber in a desired manner. The tissue penetrating proximal tips are configured to penetrate the tissue lining at an angle approximately perpendicular to a center line axis of the partitioning device. The tissue penetrating proximal tips of the ribs may be provided with barbs, hooks and the like which prevent withdrawal from the tips from the heart wall.

An expansive member such as one or more strands or swellable pads extend between at least one pair of adjacent ribs at or close to the outer edge or periphery of the membrane to exert enough pressure to the flexible membrane periphery when the partitioning device is in an expanded configuration to ensure an adequate seal between the membrane periphery and the lining of the heart wall. In one embodiment, a single strand or strands extend around essentially the entire periphery of the membrane so that the flexible periphery of the membrane between each pair of ribs is effectively sealed against the heart wall. The expansive strand or strands are formed of material which is stiffer than the flexible, unsupported material of the membrane to provide an outward expansive force or thrust to prevent formation of inwardly directed folds or wrinkles when the ribs of the partitioning device are in at least a partially contracted configuration. Suitable strand or strands are formed of material such as polypropylene suture or superelastic NiTi alloy wires. Such strands are typically about 0.005 to about 0.03 inch (0.13-0.76 mm) in diameter to provide the requisite outward expansive force when placed in a circular position such as around the periphery of the membrane in less than completely expanded configuration.

In another embodiment expandable pads are provided between each adjacent pair of ribs which are configured to swell upon contact with body fluids to provide an outward expansive force or thrust, as above, to prevent formation of inwardly directed folds or wrinkles when the ribs of the partitioning device are in at least a partially contracted configuration. Preferably the pads are formed of expansive hydrophilic foam. Suitable swellable materials includable collagen, gelatin, polylactic acid, polyglycolic acid, copolymers of polylactic acid and polyglycolic acid, polycaprolactone, mixtures and copolymers thereof. Other suitable swellable bioresorbable polymeric materials may be employed. The expandable pads may be formed so as to delivery a variety of therapeutic or diagnostic agents.

The ribs in their expanded configuration angle outwardly from the hub and the free proximal ends curve outwardly so that the membrane secured to the ribs of the expanded frame forms a trumpet-shaped, pressure receiving surface.

The partitioning membrane in the expanded configuration has radial dimensions from about 10 to about 160 mm, preferably about 25 to about 50 mm, as measured from the center line axis. The membrane is preferably formed of flexible material or fabric such as expanded polytetrafluoroethylene (ePTFE).

The partitioning device is designed to be oversized with respect to the chamber in which it is to be deployed so that the ribs of the device apply an outward force against the chamber wall. When the partitioning device is collapsed for delivery, the outwardly biased strand or strands ensures that there are no inwardly directed folds or wrinkles and that none are formed when the partitioning device is expanded for deployment within the heart chamber.

In one partitioning device design embodying features of the invention, the free ends of the expansive strand or strands may be secured together or to the partitioning device. Alternatively, in another device design, the expansive strand or strands may be long enough so that one or both free ends thereof extend out of the patient to facilitate collapse and retrieval of the partitioning device. Pulling on the free ends of the strand extending out of the patient closes the expanded portion i.e. the ribs and membrane, of the partitioning device to collapse of the device and such pulling can pull the collapsed partitioning device into the inner lumen of a guide catheter or other collecting device The reinforced partitioning component preferably includes a supporting component or stem which has a length configured to extend distally to the heart wall surface to support the partitioning device within the heart chamber. The supporting component has a plurality of pods or feet, preferably at least three, which distribute the force of the partitioning device about a region of the ventricular wall surface to avoid immediate or long term damage to the tissue of the heart wall, particularly compromised or necrotic tissue such as tissue of a myocardial infarct (MI) and the like. Pods of the support component extend radially and preferably are interconnected by struts or planes which help distribute the force over an expanded area of the ventricular surface.

The partitioning device may be delivered percutaneously or intraoperatively. One particularly suitable delivery catheter has an elongated shaft, a releasable securing device on the distal end of the shaft for holding the partitioning device on the distal end and an expandable member such as an inflatable balloon on a distal portion of the shaft proximal to the distal end to press the interior of the recess formed by the pressure receiving surface to ensure that the tissue penetrating tips or elements on the periphery of the partitioning device penetrate sufficiently into the heart wall to hold the partitioning device in a desired position to effectively partition the heart chamber. A suitable delivery device is described in co-pending application Ser. No. 10/913,608, filed on Aug. 5, 2004, and assigned to the present assignee.

The partitioning device embodying features of the invention is relatively easy to install and is a substantially improved treatment of a diseased heart. A more normal diastolic and systolic movement of a patient's diseased heart is achieved. Concomitantly, an increase in the ejection fraction of the patient's heart chamber is usually obtained. These and other advantages of the invention will become more apparent from the following detailed description of the invention and the accompanying exemplary drawings.

BRIEF DESCRIPTION OF THE DRAWINGS

FIG. 9 is a transverse cross-sectional view of the delivery system shown in FIG. 8 taken along the lines 9-9.

FIG. 10 is an elevational view, partially in section, of the hub shown in FIG. 5 being secured to the helical coil of the delivery system shown in FIG. 8.

FIG. 14 is a partial schematic view of the partitioning device shown in FIGS. 1 and 2 in a contracted configuration resulting from pulling the free ends of the expansive strand at the periphery of the reinforced membrane.

FIG. 15 is a schematic view of the contracted device shown in FIG. 14 being pulled into an expanded distal end of a receiving catheter to facilitate withdrawal of the partitioning device into a receiving catheter.

FIG. 16 is a schematic view of the contracted device shown in FIG. 14 pulled further into the inner lumen of the receiving catheter.

DETAILED DESCRIPTION OF EMBODIMENTS OF THE INVENTION

Figure 1:
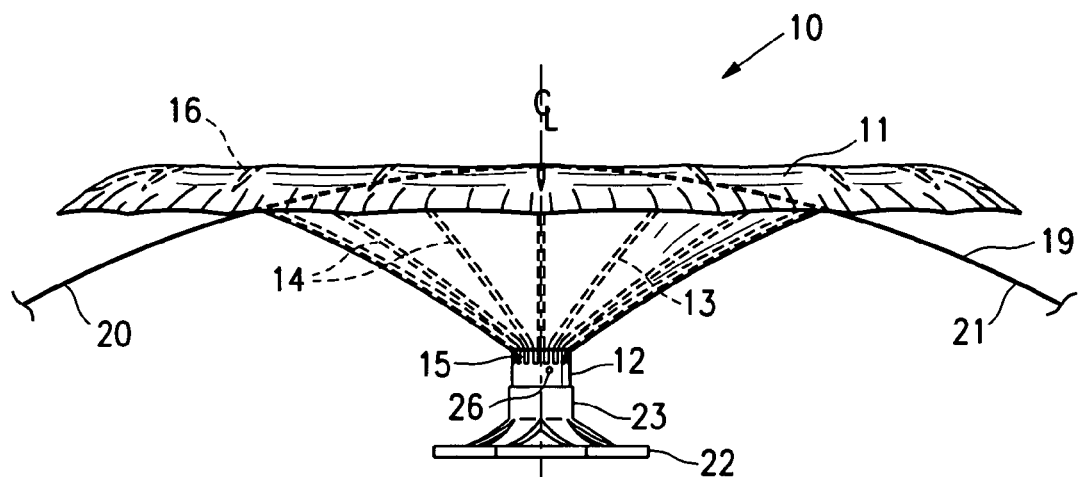
FIG. 1 is an elevational view of a partitioning device embodying features of the invention in an expanded configuration.

FIGS. 1-4 illustrate a partitioning device 10 which embodies features of the invention and which includes a partitioning membrane 11, a hub 12, preferably centrally located on the partitioning device, and a radially expandable reinforcing frame 13 is secured to the proximal or pressure side of the frame 13 as shown in FIG. 1. The ribs 14 have distal ends 15 which are secured to the hub 12 and free proximal ends 16 which are configured to curve or flare away from a center line axis. Radial expansion of the free proximal ends 16 unfurls the membrane 11 secured to the frame 13 so that the membrane presents a pressure receiving surface 17 which defines in part the productive portion of the patient's partitioned heart chamber. The peripheral edge 18 of the membrane 11 may be serrated as shown.

A continuous expansive strand 19 extends around the periphery of the membrane 11 on the pressure side thereof to apply pressure to the pressure side of the flexible material of the membrane to effectively seal the periphery of the membrane against the wall of the ventricular chamber. The ends 20 and 21 of the expansive strand 19 are shown extending away from the partitioning device in FIGS. 2 and 3. The ends 20 and 21 may be left unattached or may be secured together, e.g. by a suitable adhesive or the membrane 11 itself. While not shown in detail, the membrane 11 has a proximal layer secured to the proximal faces of the ribs 14 and a distal layer secured to the distal faces of the ribs in a manner described in co-pending application Ser. No. 10/913,608, filed on Aug. 5, 2004.

Figure 4:
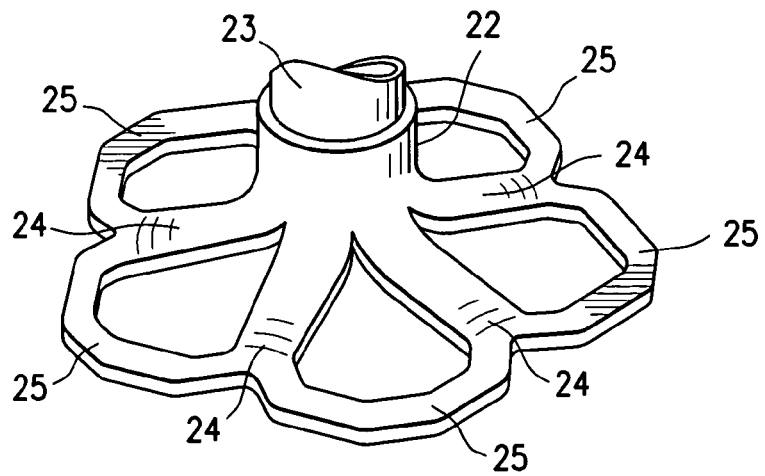
FIG. 4 is a perspective view of the non-traumatic tip of the distally extending stem of the device shown in FIG. 1.
Figure 5:
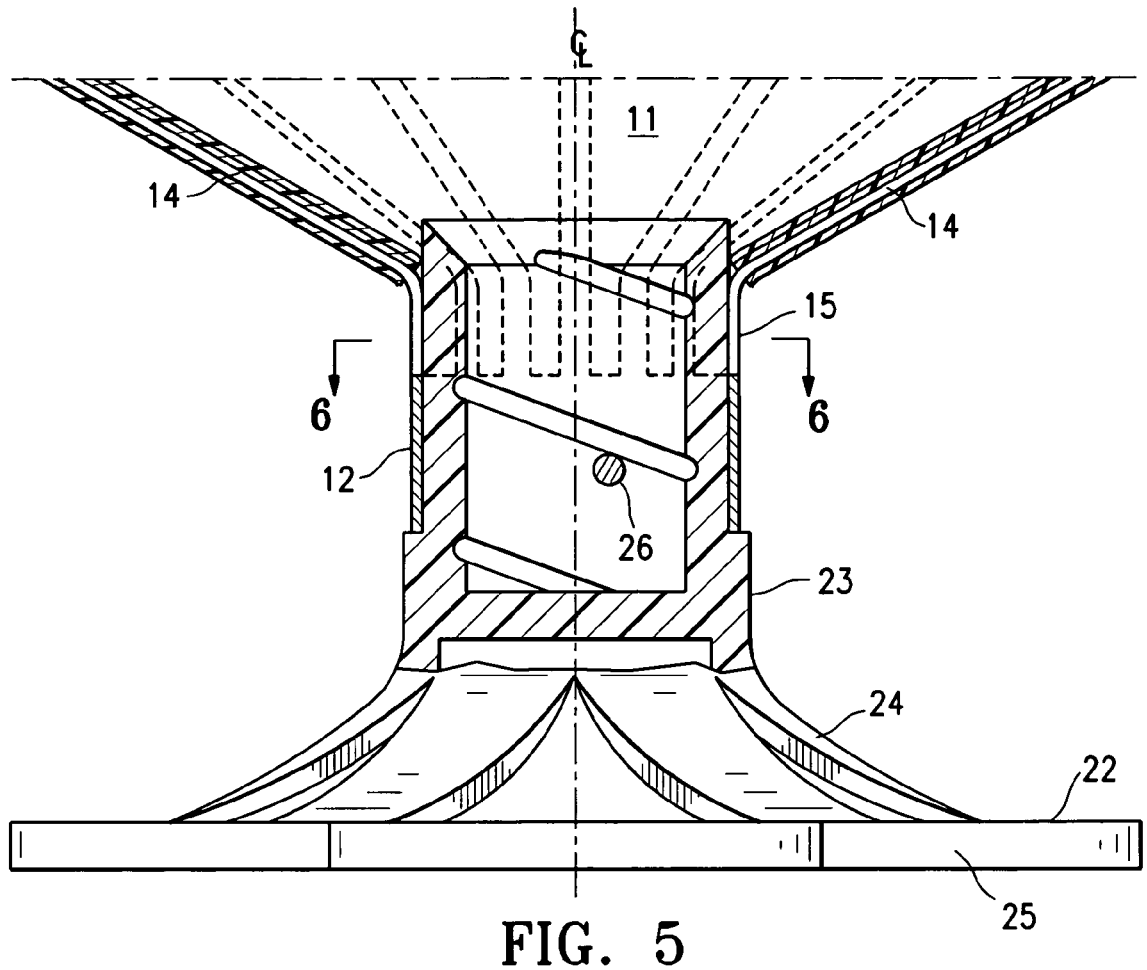
FIG. 5 is a partial cross-sectional view of the hub of the partitioning device shown in FIG. 2 taken along the lines 5-5.
Figure 8:
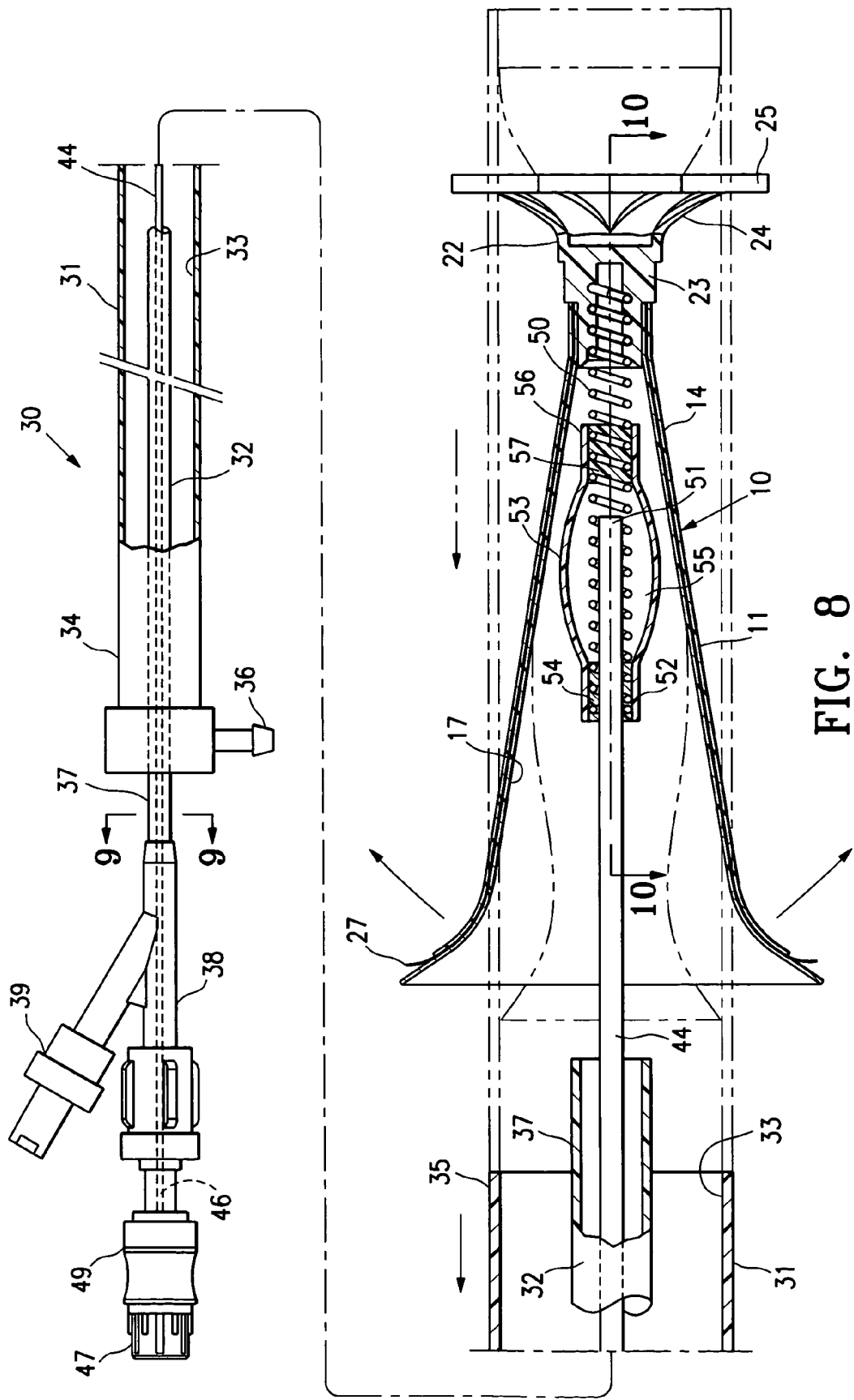
FIG. 8 is a schematic elevational view, partially in section, of a delivery system with the partitioning device shown in FIGS. 1 and 2 mounted thereon.

The hub 12 shown in FIGS. 4 and 5 preferably is connected to a non-traumatic support component 22. The support component 22 has a stem 23 a plurality of pods or feet 24 extending radially away from the center line axis and the ends of the feet 24 are secured to struts 25 which extend between adjacent feet. A plane of material (not shown) may extend between adjacent feet 24 in a web-like fashion to provide further support in addition to or in lieu of the struts 25. The inner diameter of the stem 23 is threaded to secure the partitioning device 10 to a delivery catheter as shown in FIGS. 8-10.

Figure 6:
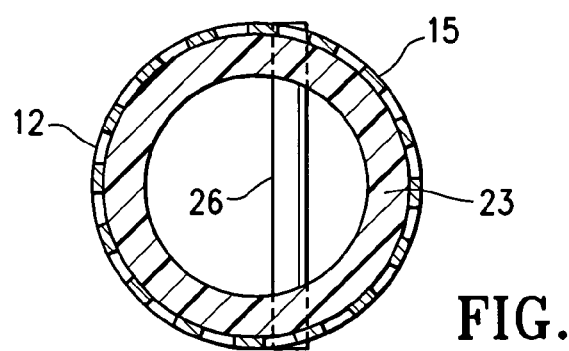
FIG. 6 is a transverse cross sectional view of the hub shown in FIG. 5 taken along the lines 6-6.

As shown in FIG. 5, the distal ends 15 of the ribs 14 are secured within the hub 12 and, as shown in FIG. 6, a transversely disposed connector bar 26 is secured within the hub which is configured to secure the hub 12 to the nontraumatic support component 22.

Figure 2:
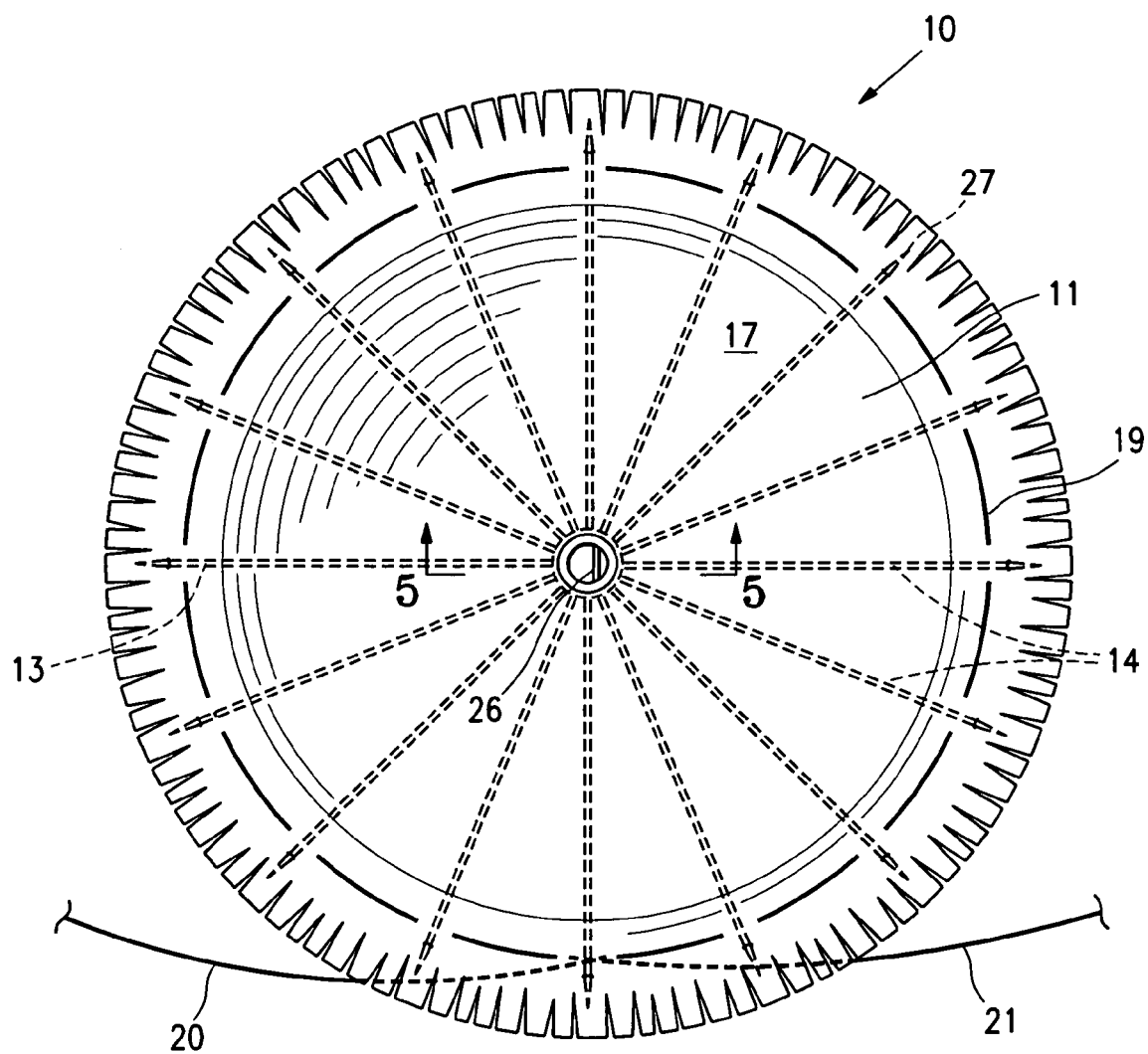
FIG. 2 is a plan view of the partitioning device shown in FIG. 1 illustrating the upper surface of the device.
Figure 3:
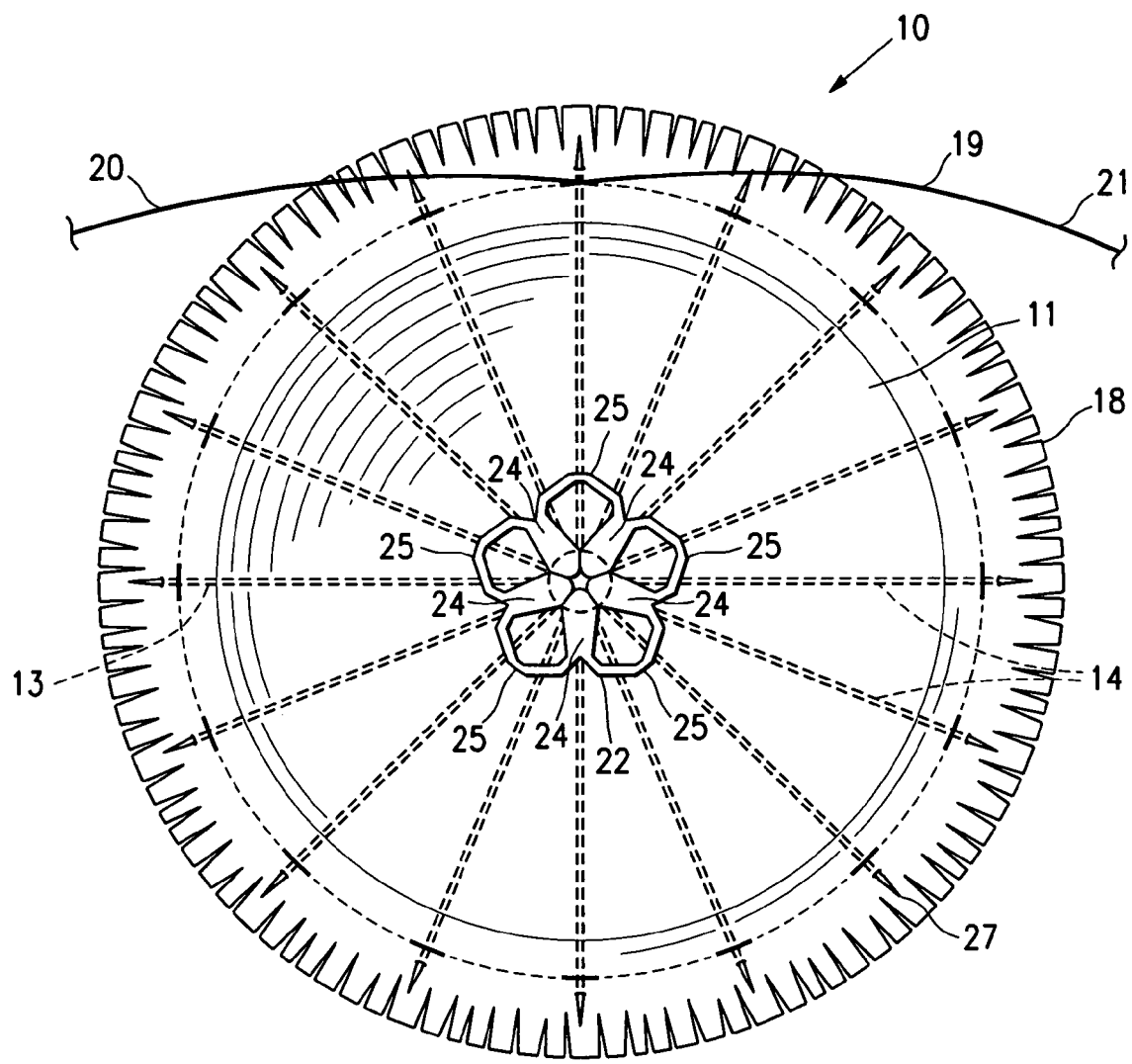
FIG. 3 is bottom view of the partitioning device shown in FIG. 1.

As illustrated in FIGS. 5 and 6, the connector bar 26 of the hub 12 allows the partitioning device 10 to be secured to the non-traumatic support component 22 and to be released from the delivery system within the patient's heart chamber. The distal ends 15 of the reinforcing ribs 14 are secured within the hub 12 in a suitable manner or they may be secured to the surface defining the inner lumen or they may be disposed within channels or bores in the wall of the hub 12. The distal end of the ribs 14 are preshaped so that when the ribs are not constrained, other than by the membrane 11 secured thereto (as shown in FIGS. 1 and 2), the free proximal ends 16 thereof expand to a desired angular displacement away from the centerline axis which is about 20° to about 90°, preferably about 50° to about 80°. The unconstrained diameter of the partitioning device 10 should be greater than the diameter of the heart chamber at the deployed location of the partitioning device so that an outward force is applied to the wall of the heart chamber by the partially expanded ribs 14 during systole and diastole so that the resilient frame 13 augments the heart wall movement.

Figure 7:
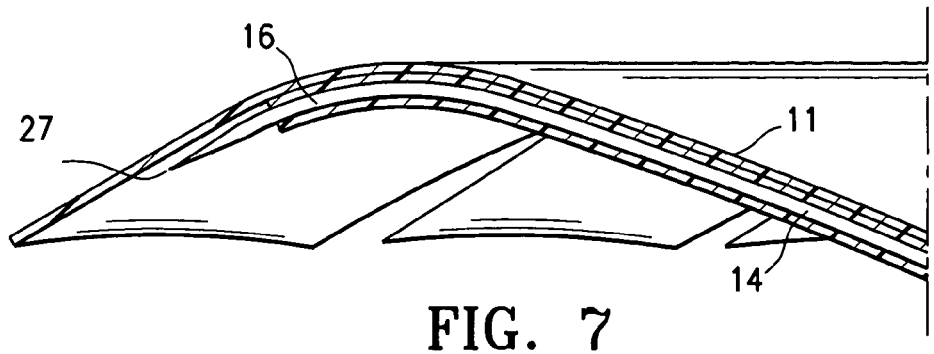
FIG. 7 is a longitudinal view, partially in section of a reinforcing rib and membrane at the periphery of the partitioning device shown in FIG. 1.

FIG. 7 illustrates the curved free proximal ends 16 of ribs 14 which are provided with sharp tip elements 27 configured to engage and preferably penetrate into the wall of the heart chamber and hold the partitioning device 10 in a deployed position within the patient's heart chamber so as to partition the ventricular chamber into a productive portion and a non-productive portion.

FIGS. 8-10 illustrate a suitable delivery system 30 delivering the partitioning device 10 shown in FIGS. 1 and 2 into a patient's heart chamber and deploying the partitioning device to partition the heart chamber as shown in FIGS. 11A-11E. The delivery system 30 includes a guide catheter 31 and a delivery catheter 32.

The guide catheter 31 has an inner lumen 33 extending between the proximal end 34 and distal end 35. A hemostatic valve (not shown) may be provided at the proximal end 34 of the guide catheter 31 to seal about the outer shaft 37 of the delivery catheter 32. A flush port 36 on the proximal end 34 of guide catheter 31 is in fluid communication with the inner lumen 33.

The delivery catheter 32 has an outer shaft 37 with an adapter 38 on the proximal end thereof having a proximal injection port 39 which is in fluid communication with the interior of the shaft 37. As shown in more detail in FIG. 9, the outer shaft 37 has an inner shaft 41 which is disposed within the interior thereof and is secured to the inner surface of the outer shaft 37 by webs 43 which extend along a substantial length of the inner shaft. The injection port 39 is in fluid communication with the passageways 42 between the inner and outer shafts 41 and 37 respectively and defined in part by the webs 43. A torque shaft 44, which is preferably formed of hypotubing (e.g. formed of stainless steel or superelastic NiTi), is disposed within the inner lumen 45 of the inner shaft 41 and has a proximal end 46 secured within the adapter 38. Balloon inflation port 47 is in fluid communication with the inner lumen 48 of the torque shaft 44. Torque shaft 44 is rotatably disposed within the inner lumen 45 of the inner shaft 41 and is secured to rotating knob 49. A helical coil screw 50 is secured to the distal end 51 of the torque shaft 44 and rotation of the torque knob 49 on the proximal end 46 of the torque shaft 44 rotates the screw 50 to facilitate deployment of a partitioning device 10. The proximal end 52 of inflatable balloon 53 is sealingly secured by adhesive 54 about the torque shaft 44 proximal to the distal end 51 of the torque shaft. The balloon 53 has an interior 55 in fluid communication with the inner lumen 48 of the torque shaft 44. Inflation fluid may be delivered to the balloon interior 55 through port 47 which is in fluid communication with the inner lumen 48 of the torque shaft 44. The distal end 56 of the balloon 53 is sealingly secured by adhesive 57 to the helical screw 50. The proximal and distal ends 52 and 56 of the balloon 53 are blocked by the adhesive masses 54 and 57 to prevent the loss of inflation fluid delivered to the interior 55 of the balloon 53. Delivery of inflation fluid through a fluid discharge port 58 in the distal end 51 of the torque shaft 44 inflates the balloon 53 which in turn applies pressure to the Proximal surface of the partitioning device 10 to facilitate securing the partitioning component 10 to the wall 59 of heart chamber 60 as shown in FIGS. 11A-11E discussed below.

Figure 11A:
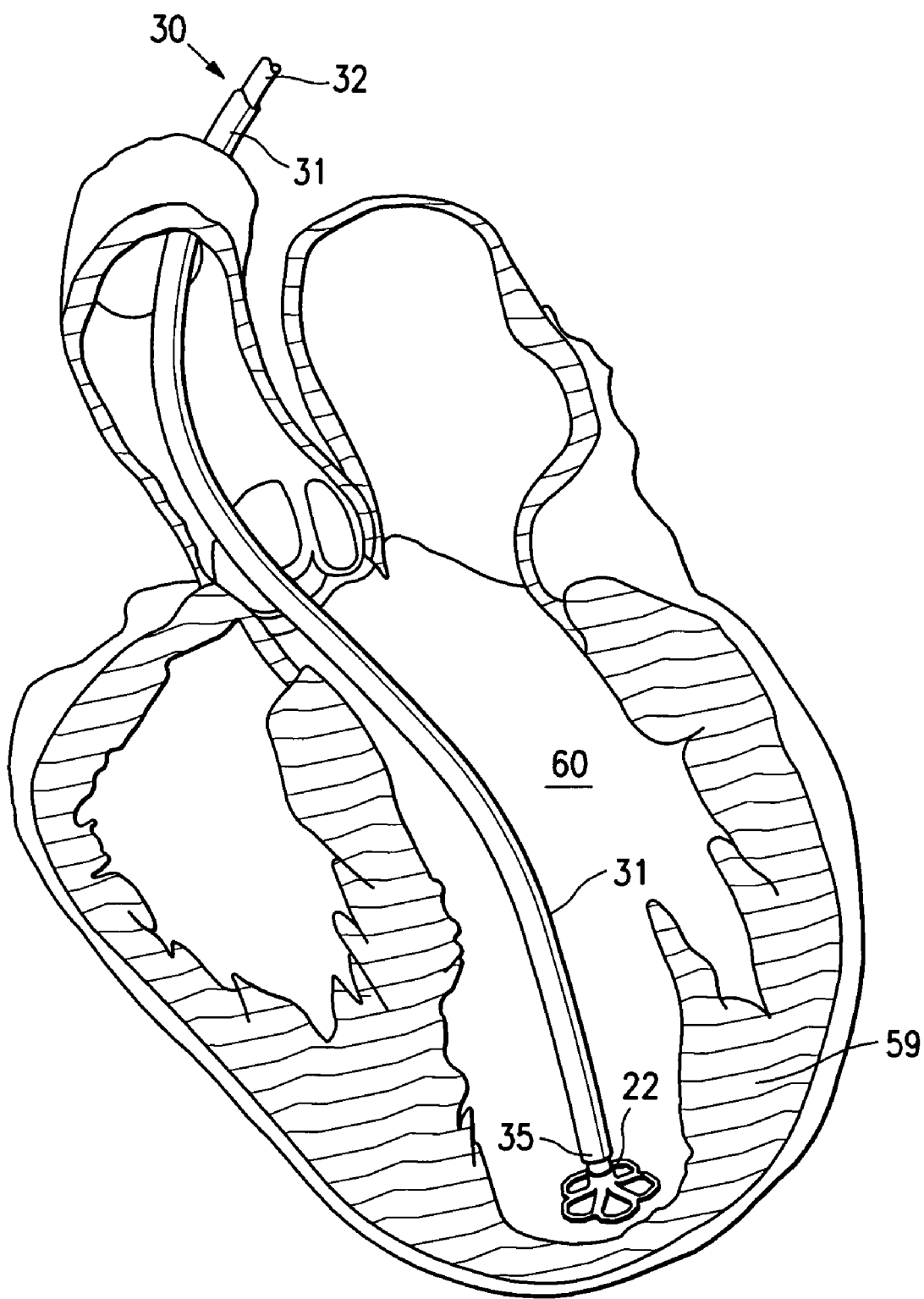
FIGS. 11A-11E are schematic views of a patient's left ventricular chamber illustrating the deployment of the partitioning device shown in FIGS. 1 and 2 with the delivery system shown in FIG. 8 to partition a patient's heart chamber (left ventricle) into a primary productive portion and a secondary, non-productive portion.

As shown in FIG. 11A, the partitioning component 10 is delivered through a delivery system 30 which includes a guide catheter 31 and a delivery catheter 32. The partitioning component 10 is collapsed in a first, delivery configuration which has small enough transverse dimensions to be slidably advanced through the inner lumen 33 of the guide catheter 31. Preferably, the guide catheter 31 has been previously percutaneously introduced and advanced through the patient's vasculature, such as the femoral artery, in a conventional manner to the desired heart chamber 60. The delivery catheter 32 with the partitioning component 10 attached is advanced through the inner lumen 33 of the guide catheter 31 until the partitioning component 10 is ready for deployment from the distal end of the guide catheter 31 into the patient's heart chamber 60 to be partitioned.

Figure 11B:
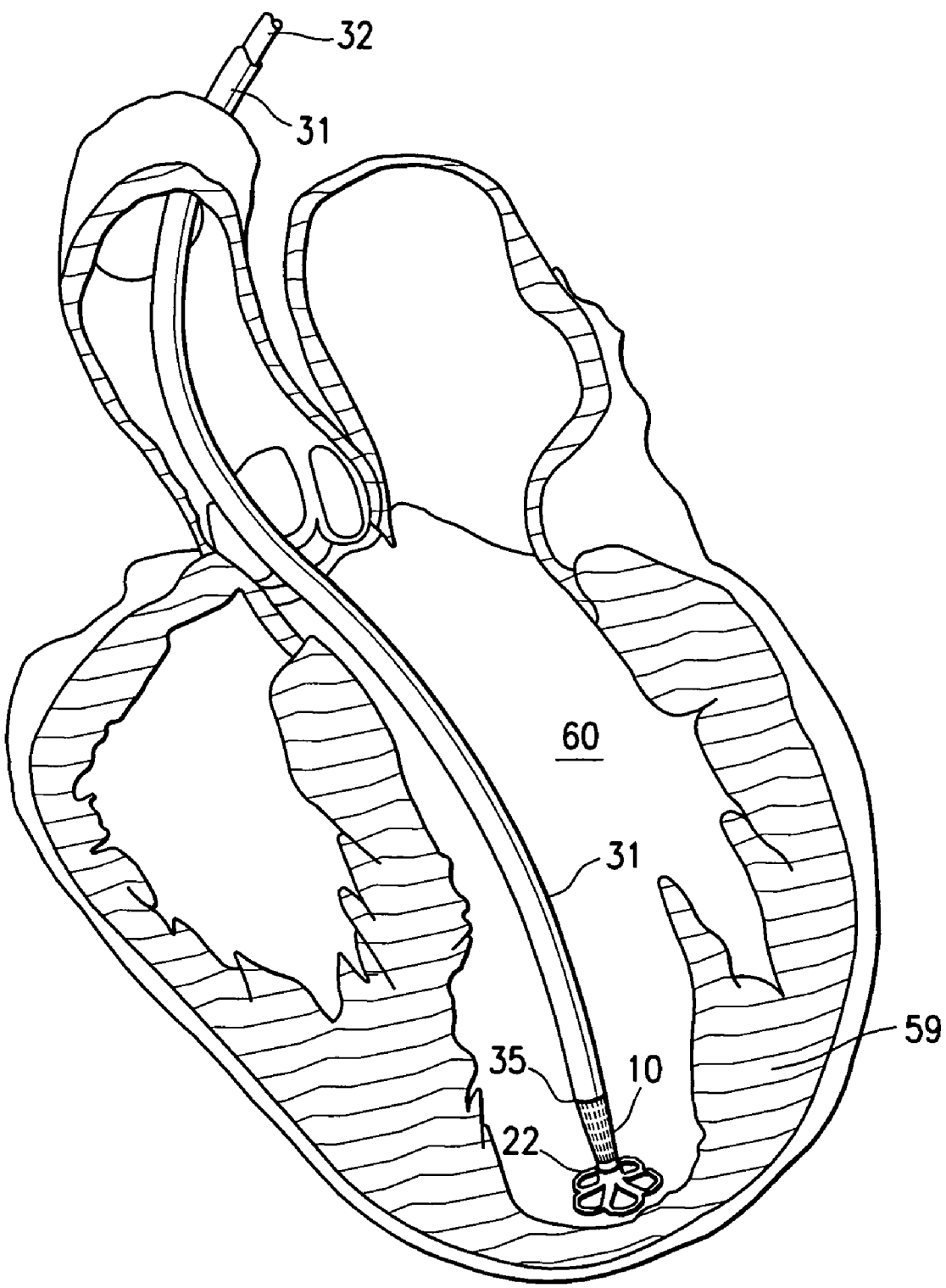
Figure 11C:
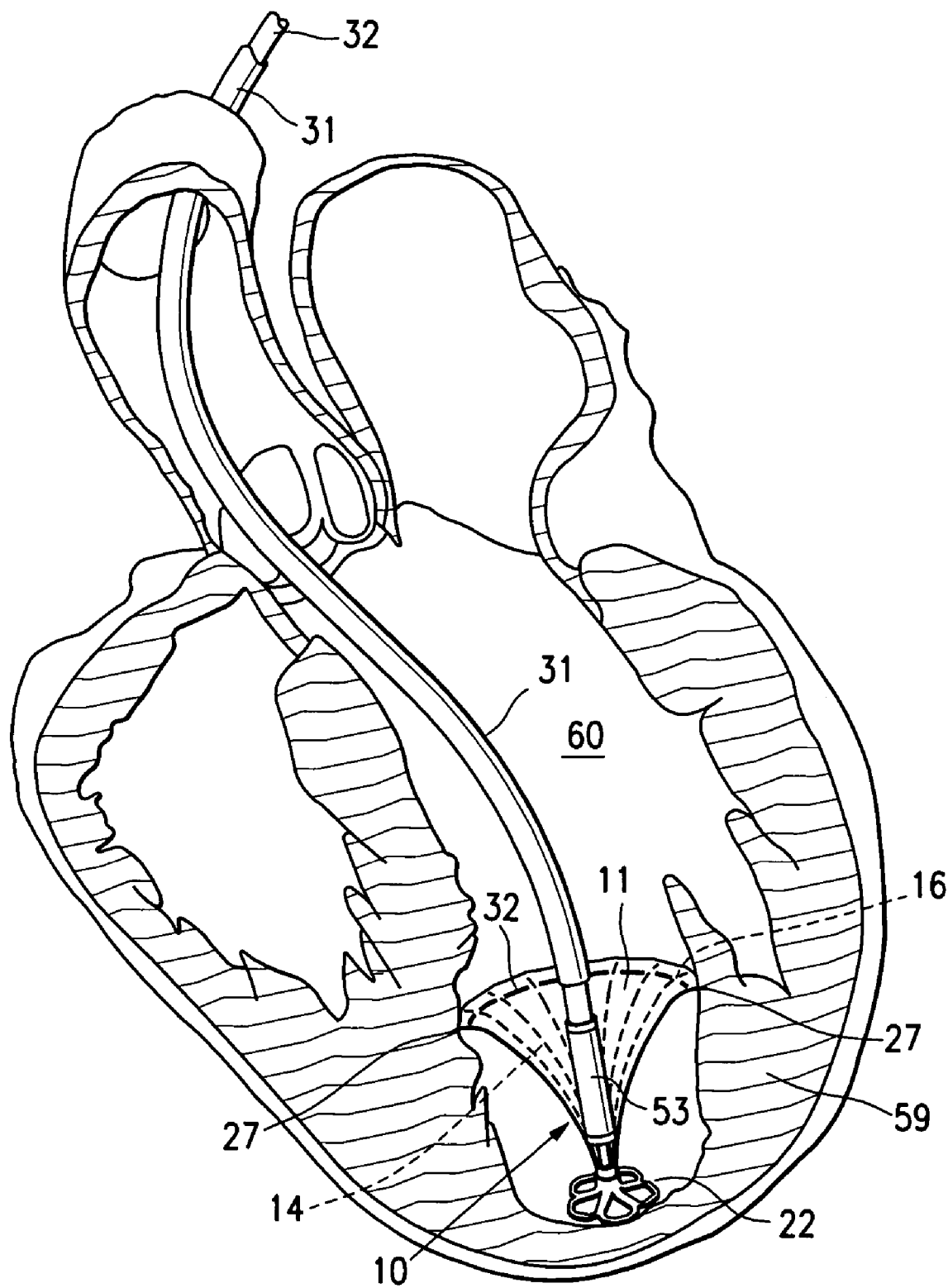

As shown in FIG. 11B, the partitioning component 10 mounted on the screw 50 is urged further out of the inner lumen 33 of the guide catheter 32 until the support component 22 engages the heart wall 59. The guide catheter 31 is withdrawn while the delivery catheter 32 is held in place until the proximal ends 16 of the ribs 14 exit the distal end 35 of the guide catheter. As shown in FIG. 11C, the free proximal ends 16 of ribs 14 expand outwardly to press the sharp proximal tips 27 of the ribs 14 against and preferably into the tissue lining the heart wall 59.

Figure 11D:
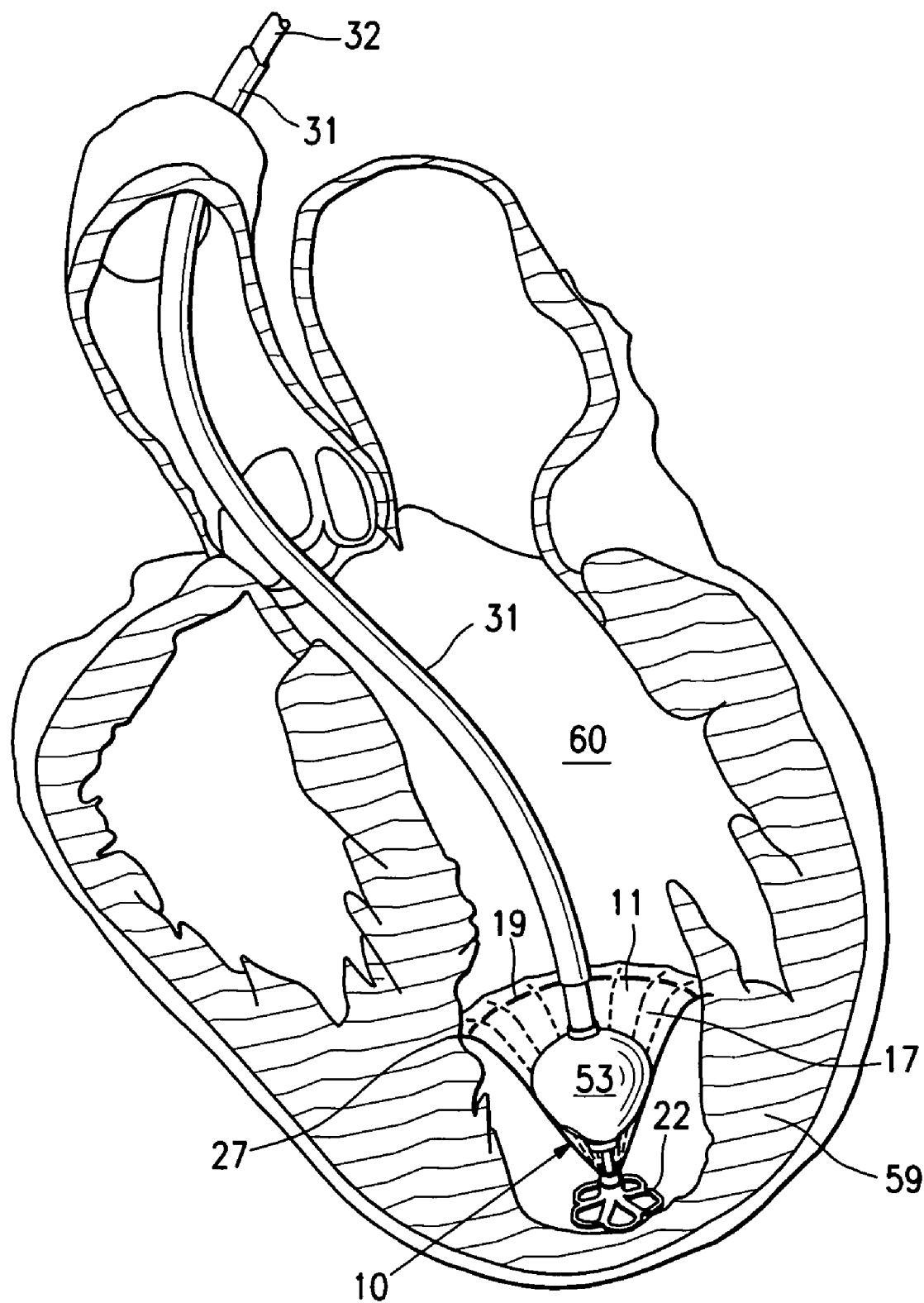

With the partitioning component 10 deployed within the heart chamber 60 and preferably partially secured therein, inflation fluid is introduced through the inflation port 58 in the distal end 51 torque shaft 44 where it is directed into the balloon interior 54 to inflate the balloon 53. The inflated balloon 53 presses against the pressure receiving surface 17 of the membrane 11 of the partitioning component 10 to ensure that the sharp proximal tips 27 are pressed well into the tissue lining the heart wall 59 as shown in FIG. 11D.

With the partitioning device 10 properly positioned within the heart chamber 60, the knob 49 on the torque shaft 44 (as shown in FIG. 8) is rotated counter-clockwise to disengage the helical coil screw 50 of the delivery catheter 32 from the stem 23 secured within hub 12. The counter-clockwise rotation of the torque shaft 44 rotates the helical coil screw 50 which rides on the connector bar 26 secured within the hub 12. Once the helical coil screw 50 disengages the connector bar 26, the delivery system 30, including the guide catheter 31 and the delivery catheter 32, may then be removed from the patient.

The proximal end 34 of the guide catheter 31 is provided with a flush port 36 to inject fluids such as therapeutic, diagnostic or other fluids through the inner lumen 33 during the procedure. Similarly, the proximal injection port 39 of adapter 38 is in communication with passageways 42 if the delivery catheter 32 for essentially the same purpose.

Figure 11E:
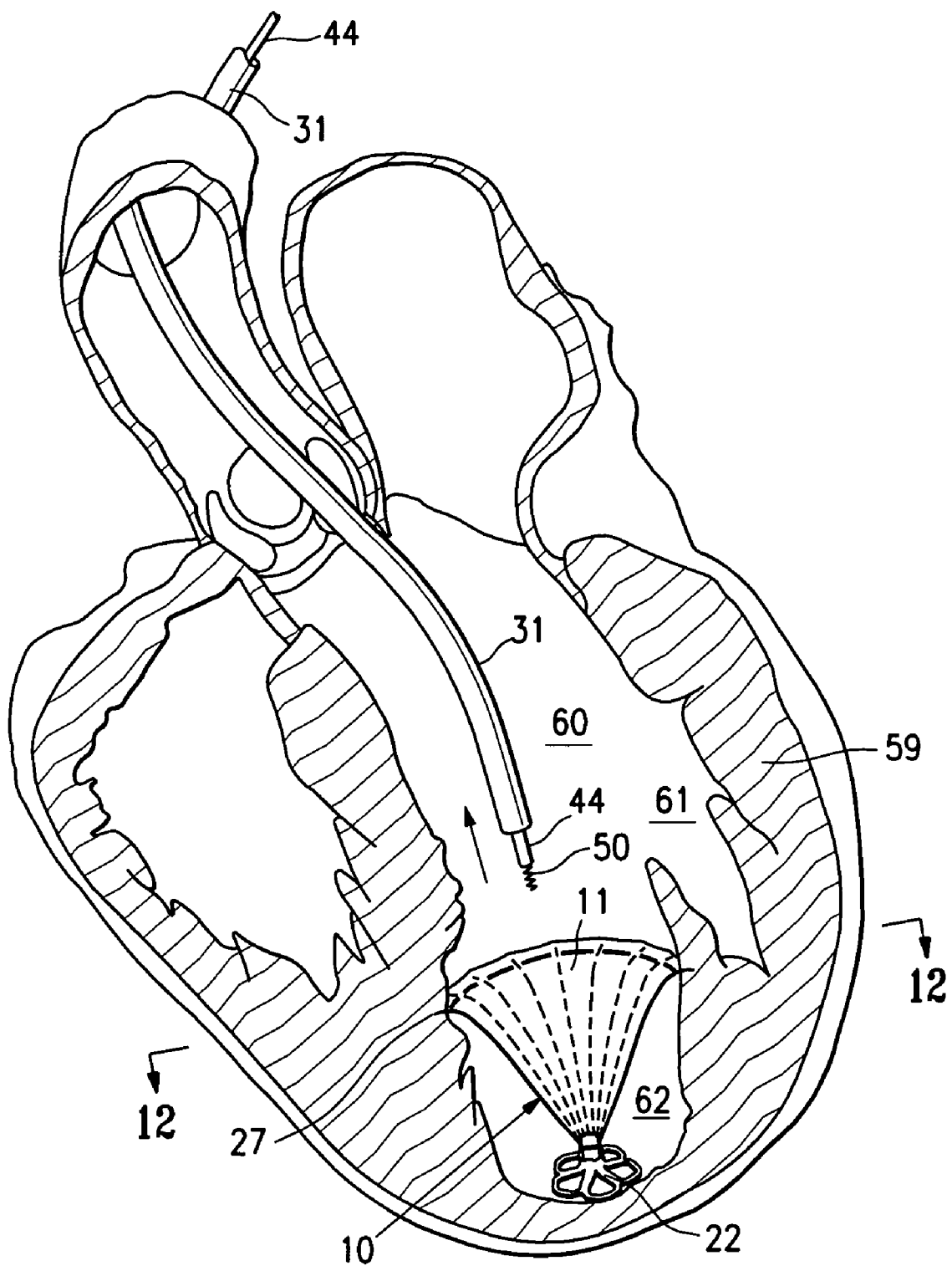

The deployment of the partitioning component 10 in the patient's heart chamber 60 as shown in FIG. 11E divides the chamber into a main productive or operational portion 61 and a secondary, essentially non-productive portion 62. The operational portion 61 is smaller than the original heart chamber 60 and provides for an improved ejection fraction and an improvement in blood flow. Over time, the non-productive portion 62 fills first with thrombus and subsequently with cellular growth. Bio-resorbable fillers such as polylactic acid, polyglycolic acid, polycaprolactone and copolymers and blends may be employed to initially fill the non-productive portion 62. Fillers may be suitably supplied in a suitable solvent such as dimethylsulfoxide (DMSO). Other materials which accelerate tissue growth or thrombus may be deployed in the non-productive portion 62 as well as non-reactive fillers.

Figure 12:
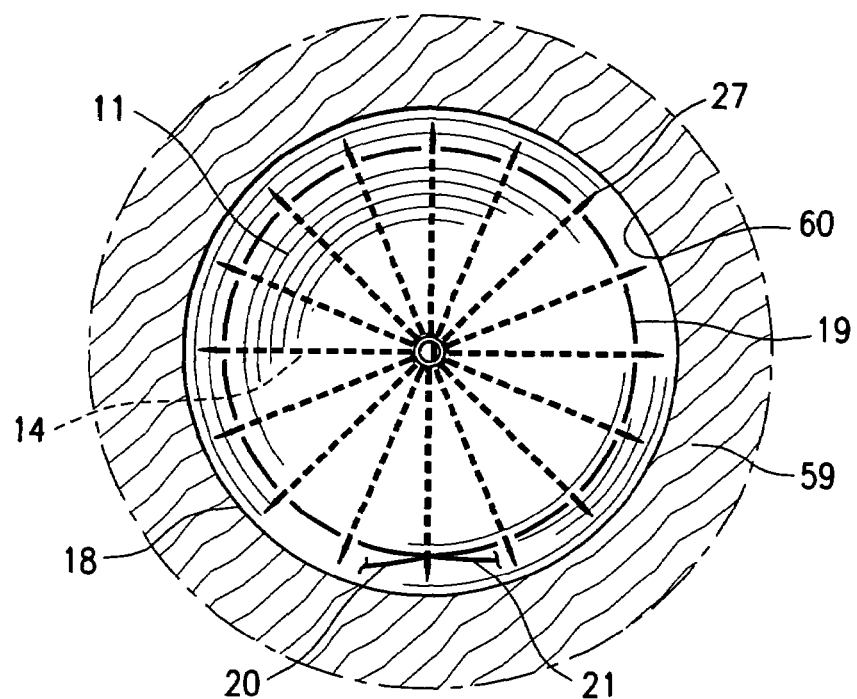
FIG. 12 is a schematic plan view of the deployed device shown in FIG. 11E within a patient's heart chamber.
Figure 13:
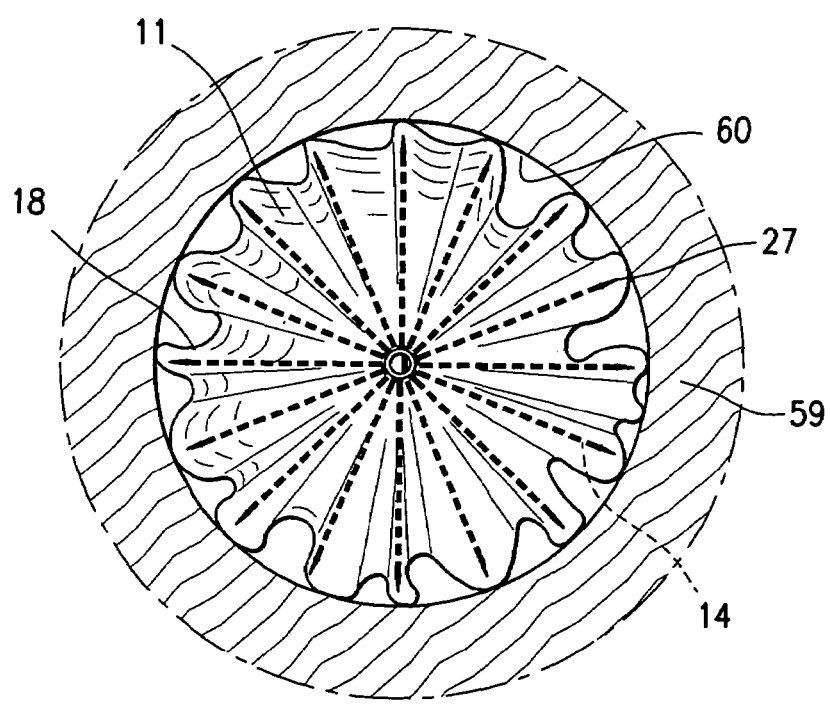
FIG. 13 is a schematic plan view of the partitioning device shown in FIG. 1 without the expansive strand after deployment within a patient's heart chamber.

FIG. 12 is a top view of the deployed partitioning device shown in FIG. 11E schematically illustrating the sealed periphery of the membrane 11 against the ventricular wall. This is to be compared with the schematic presentation shown in FIG. 13 which illustrates a partitioning device without a strand having folds along the periphery 18 which do not allow for an effective seal against the wall 59 of the heart chamber 60.

The partitioning device 10 may be conveniently formed by the method described in co-pending application Ser. No. 10/913,608, filed on Aug. 5, 2004, which is incorporated herein by reference.

While porous ePTFE material is preferred, the membrane 11 may be formed of suitable biocompatible polymeric material which includes Nylon, PET (polyethylene terephthalate) and polyesters such as Hytrel. The membrane 11 may be foraminous in nature to facilitate tissue ingrowth after deployment within the patient's heart. The delivery catheter 32 and the guiding catheter 31 may be formed of suitable high strength polymeric material such as PEEK (polyetheretherketone), polycarbonate, PET, Nylon, and the like. Braided composite shafts may also be employed.

FIGS. 14-16 illustrate the collapse and retrieval of a partitioning device 10 by pulling on the ends 20 and 21 of the expansive strand 19 which extends around the periphery of the membrane 11. Typically, the partitioning device 10 would still be secured to the delivery catheter 32, but the delivery catheter is not shown to simplify the drawings. In FIG. 14 the partitioning device 10 is shown in a partially collapsed configuration. In FIG. 15 the partially collapsed partitioning device 10 is shown being withdrawn into the flared distal end 63 of retrieval catheter 64. FIG. 16 illustrates the completely collapsed partitioning device 10 pulled further into the retrieval catheter 64. The partitioning device 10 may be withdrawn by pulling the device through the inner lumen 65 of the retrieval catheter 64. Optionally, the partitioning device 10 and retrieval catheter may be withdrawn from the patient together.

To assist in properly locating the device during advancement and placement thereof into a patient's heart chamber, parts, e.g. the distal extremity, of one or more of the ribs 14 and/or the hub 12 may be provided with markers at desirable locations that provide enhanced visualization by eye, by ultrasound, by X-ray, or other imaging or visualization means. Radiopaque markers may be made with, for example, stainless steel, platinum, gold, iridium, tantalum, tungsten, silver, rhodium, nickel, bismuth, other radiopaque metals, alloys and oxides of these metals.

Figure 17:
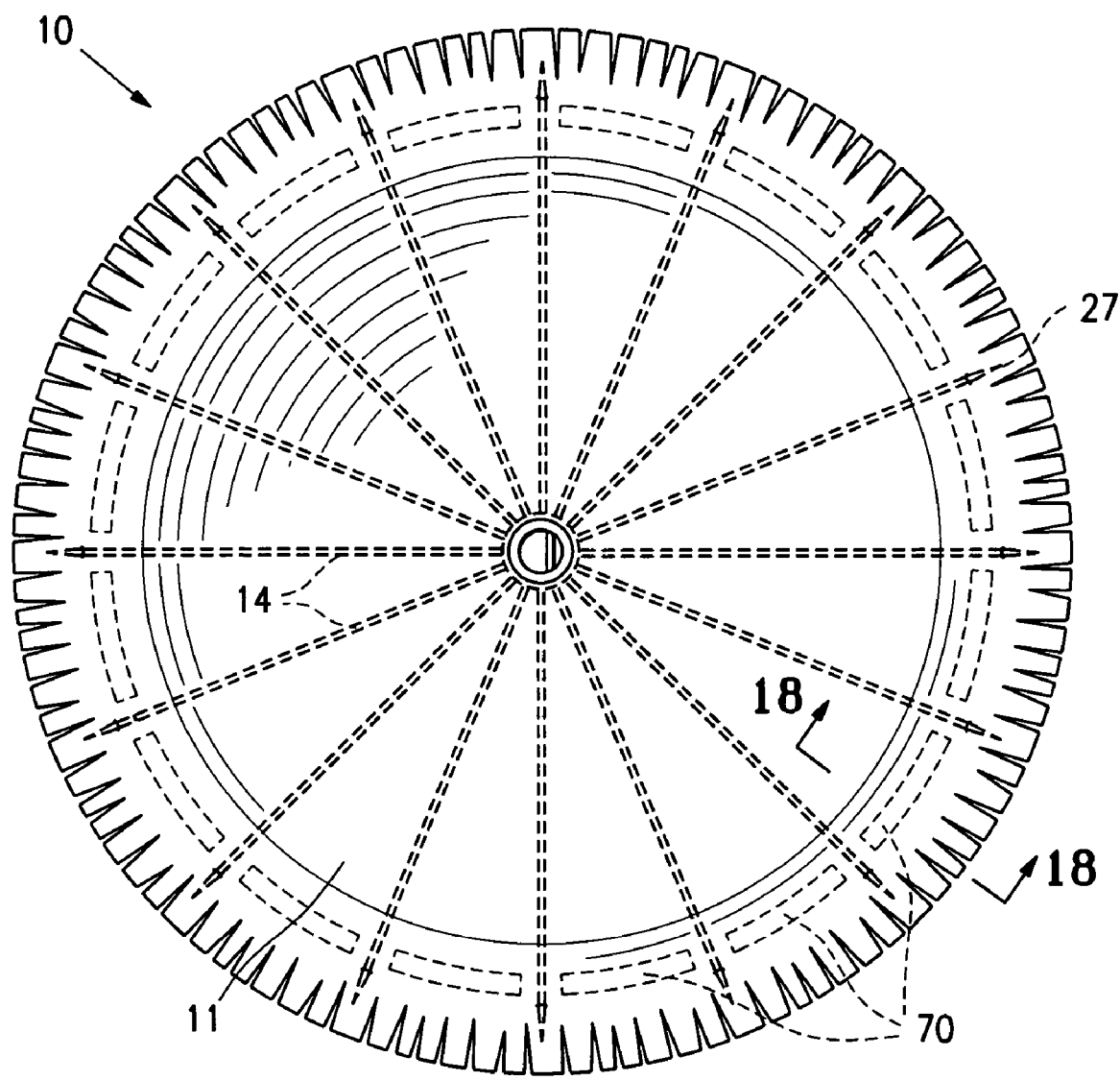
FIG. 17 is a plan view of the top of an alternative partitioning device which has swellable pads disposed between adjacent ribs to press the membrane between the ribs against the heart wall.
Figure 18:
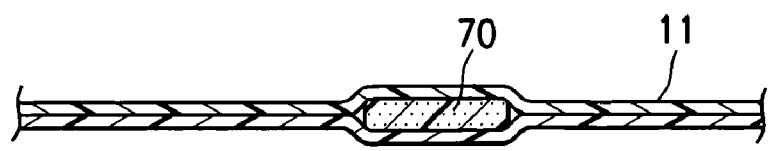
FIG. 18 is a cross-sectional view of a swellable pad disposed between Two membrane layers secured to the ribs of the partitioning device taken on line 18-18 of FIG. 17.

FIGS. 17 and 18 illustrate an alternative design which embodies features of the invention in which the partitioning device 10 is provided with swellable bodies 70, preferably hydrophilic foam, around the periphery of the membrane 11 between adjacent ribs 14. When these bodies contact body fluid, such as blood, upon deployment, they swell, thereby sealing the peripheral portion of the membrane 11 against the patient's heart wall as previously described. The details of the partitioning device 10 are essentially the same as in the previous embodiment and elements in this alternative embodiment are given the same reference numbers as similar elements in the previous embodiments.

To the extent not otherwise described herein, the various components of the partitioning device and delivery system may be formed of conventional materials and in a conventional manner as will be appreciated by those skilled in the art.

While particular forms of the invention have been illustrated and described herein, it will be apparent that various modifications and improvements can be made to the invention. Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is intended that this invention to be defined by the scope of the appended claims as broadly as the prior art will permit.

Terms such a "element", "member", "component", "device", "section", "portion", "step", "means" and words of similar import, when used herein shall not be construed as invoking the provisions of 35 U.S.C. §112(6) unless the following claims expressly use the term "means" followed by a particular function without specific structure or the term "step" followed by a particular function without specific action. Accordingly, it is not intended that the invention be limited, except as by the appended claims. All patents and patent applications referred to herein are hereby incorporated by reference in their entirety.

What is claimed is:

1. A device for treating a patient by partitioning a chamber of the patient's heart into a primary productive portion and a secondary non-productive portion, the device comprising:
   an expandable frame formed of a plurality of ribs having distal ends secured to a central hub and free, outwardly flared, proximal ends,
   a pressure receiving membrane formed at least in part of flexible material, the membrane forming a recess in an expanded, deployed configuration, wherein the membrane comprises a loose and flexible peripheral region configured to seal to a ventricular wall surface to partition the ventricle and create the secondary non-productive portion, wherein the flexible peripheral region of the membrane comprises notched serrations; and
   an outwardly biased member which is secured to the membrane at a position that is radially inward from the loose peripheral region of the membrane, wherein the outwardly biased member is configured to stiffen at least a portion of the membrane so as to reduce wrinkling of the membrane so that the peripheral region of the membrane may seal against a ventricular wall surface defining in part the heart chamber.

2. The device of claim 1 wherein the outwardly biased member is an elongated strand.

3. The device of claim 2 wherein the strand extends about essentially the entire membrane periphery.

4. The device of claim 1 wherein the outwardly biased member is a swellable body.

5. The device of claim 4 wherein the swellable body is hydrophilic.

6. The device of claim 1 wherein the outwardly biased member extends between adjacent ribs of the expandable frame.

7. The device of claim 1 wherein the flexible material of the membrane is formed at least in part of expanded fluoropolymer.

8. The device of claim 7 wherein the expanded fluoropolymer is polytetrafluoroethylene.

9. The device of claim 1 wherein the flexible material of the membrane is formed at least in part of a polymeric fabric.

10. A device for treating a patient's heart by partitioning a chamber of the patient's heart into a primary productive portion and a secondary non-productive portion, comprising:
    an expandable frame formed of a plurality of ribs having secured first ends and free second ends;
    a membrane secured to the frame, wherein the membrane forms a recess when in an expanded deployed configuration, further wherein the membrane comprises a loose and flexible peripheral region configured to seal to a ventricular wall surface to partition the ventricle and create the secondary non-productive portion, wherein the peripheral region of the membrane comprises notched serrations; and
    at least one outwardly biased member which is secured to the membrane at a position that is radially inward from the loose peripheral region of the membrane, wherein the outward biased member is configured to stiffen at least a portion of the membrane so as to reduce wrinkling of the membrane, so that the peripheral region of the membrane may seal against a ventricular wall surface defining in part the patient's heart chamber.

11. The device of claim 10 wherein the expandable frame has a central hub and the first ends of the ribs are secured to the central hub.

12. The device of claim 11 wherein the central hub has a stem with a non-traumatic distal tip configured to engage a region of a ventricular wall defining in part the non-productive portion thereof.

13. The device of claim 12 wherein the non-traumatic distal tip has at least three feet that extend radially from a centerline axis.

14. The device of claim 13 wherein feet of the non-traumatic distal tip have ends that are flexibly interconnected.

15. The device of claim 14 wherein the ends of the feet are flexibly interconnected by struts or webs.

16. The device of claim 14 wherein the ends of the feet are in an essentially common plane.

17. The device of claim 10 wherein the at least one outwardly biased member extends about essentially the entire periphery of the membrane.

18. The device of claim 10 wherein the at least one outwardly biased member is a strand.

19. The device of claim 18 wherein the strand is formed of suture material.

20. The device of claim 18 wherein the strand is formed of polypropylene or superelastic NiTi alloy.

21. The device of claim 10 wherein the one or more outwardly biased members are swellable bodies on the periphery of the membrane.

22. The device of claim 21 wherein the swellable body is formed of a bioabsorbable material.

23. The device of claim 22 wherein the bioabsorbable material is selected from the group consisting of collagen, gelatin, polylactic acid, polyglycolic acid, copolymers of polylactic acid and polyglycolic acid, polycaprolactone, mixtures and copolymers thereof.

24. The device of claim 10 wherein the expandable frame is self expanding.

25. The device of claim 24 wherein the ribs of the expandable frame are formed of superelastic NiTi alloy which is in an austenite phase when unstressed at body temperature.

26. The device of claim 10 wherein ribs of the expandable frame have a contracted configuration for delivery to patient's heart chamber to be partitioned.

27. The device of claim 26 wherein the ribs of the expandable frame are configured to be at least in part in a stress maintained martensite phase when in the contracted configuration.

28. The device of claim 26 wherein the ribs of the expandable frame are configured to be at least in part in an austenite phase when deployed within the patient's heart chamber.

29. The device of claim 10 wherein the membrane is formed at least in part of flexible material.

30. The device of claim 29 wherein the flexible material of the membrane is formed at least in part of expanded fluoropolymer.

31. The device of claim 30 wherein the expanded fluoropolymer is expanded polytetrafluoroethylene.

32. The device of claim 10 wherein at least one outwardly biased member is secured to a portion of the membrane extending between adjacent ribs.

33. The device of claim 10 wherein the membrane has a first membrane layer secured to proximal faces of the ribs.

34. The device of claim 33 wherein the membrane has a second membrane layer secured to distal faces of the ribs.

35. The device of claim 33 wherein the first membrane layer is configured to receive pressure.

36. The device of claim 33 wherein the first membrane layer has a pressure receiving surface with radial dimensions from a center line axis of about 5 to about 80 mm.

37. The device of claim 10 wherein the first ends of the ribs are secured to a central hub.

38. The device of claim 10 wherein the free end of at least one of the ribs has a tissue penetrating securing element.

39. The device of claim 10 wherein the free end of at least one of the ribs are outwardly curved.

40. The device of claim 39 wherein the outwardly curved free ends of the ribs have tips which are configured to penetrate tissue lining the heart chamber at an angle of not more than 45° away from a center line axis of the partitioning device.

41. The device of claim 10 wherein the secured ends of the ribs are configured to facilitate abduction of the free ends of the ribs away from a centerline axis to facilitate expansion of the membrane to an expanded configuration to facilitate deployment within the patient's heart chamber.

42. The device of claim 10 wherein the expandable frame has about 3 to about 30 ribs.

43. The device of claim 10 wherein the expandable frame has about 6 to about 16 ribs.

44. The device of claim 10 wherein a first outwardly biased member extends between a first pair of adjacent ribs and a second outwardly biased member extends between a second pair of adjacent ribs.

\* \* \* \* \*

UNITED STATES PATENT AND TRADEMARK OFFICE
CERTIFICATE OF CORRECTION

PATENT NO. : 7,582,051 B2
APPLICATION NO. : 11/151164
DATED : September 1, 2009
INVENTOR(S) : Khairkhahan et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 930 days.

Signed and Sealed this

Fourteenth Day of September, 2010

David J. Kappos
*Director of the United States Patent and Trademark Office*